(12) United States Patent
Bongaerts et al.

(10) Patent No.: US 9,644,684 B2
(45) Date of Patent: May 9, 2017

(54) CAPACITANCE MEASUREMENT IN A BEARING HOUSING

(71) Applicants: Jeroen Bongaerts, GK Hilversum (NL); Florin Tatar, GE Delft (NL)

(72) Inventors: Jeroen Bongaerts, GK Hilversum (NL); Florin Tatar, GE Delft (NL)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/082,835

(22) Filed: Mar. 28, 2016

(65) Prior Publication Data
US 2016/0281788 A1 Sep. 29, 2016

(30) Foreign Application Priority Data
Mar. 27, 2015 (GB) .................................. 1505264.0

(51) Int. Cl.
*F16C 41/00* (2006.01)
*G01N 33/28* (2006.01)
*G01N 27/22* (2006.01)
*F16C 33/66* (2006.01)

(52) U.S. Cl.
CPC .......... *F16C 41/00* (2013.01); *F16C 33/6603* (2013.01); *F16C 33/6622* (2013.01); *G01N 27/22* (2013.01); *G01N 27/221* (2013.01); *G01N 33/2847* (2013.01); *G01N 33/2888* (2013.01); *F16C 2233/00* (2013.01)

(58) Field of Classification Search
CPC ........................... F16C 41/007; F16C 2233/00
See application file for complete search history.

(56) References Cited

U.S. PATENT DOCUMENTS

| | | | |
|---|---|---|---|
| 6,196,057 B1 * | 3/2001 | Discenzo | F16C 19/52 422/82.01 |
| 6,295,863 B1 * | 10/2001 | Ginder | G01M 3/04 403/27 |
| 9,080,926 B2 * | 7/2015 | Murray | G01M 13/04 |

FOREIGN PATENT DOCUMENTS

| | | | | |
|---|---|---|---|---|
| JP | 2007198576 A | * | 8/2007 | |
| NL | WO 2005033535 A1 | * | 4/2005 | ............. F16C 19/52 |

* cited by examiner

*Primary Examiner* — Thomas R. Hannon
(74) *Attorney, Agent, or Firm* — Bryan Peckjian; SKF USA Inc. Patent Dept.

(57) ABSTRACT

A bearing arrangement having a bearing mounted in a housing, wherein a grease lubricant is present within the housing for lubricating the bearing, a support frame at least partly made of an electrically insulating material, arranged in a space within the housing that lies axially between the bearing and a housing seal. The support frame includes at least one electrode pair having first and second electrodes arranged to enable grease lubricant to contact therewith. A capacitance meter provided for measuring a capacitance between the first and second electrodes. The support frame provides a radially oriented surface and a plurality of ribs that extend in a radially inward direction, the ribs having sufficient circumferential spacing to enable grease to flow between adjacent ribs. One of the first and second electrodes is provided on the radially oriented surface of the support frame or on a rib surface that faces an adjacent rib.

12 Claims, 3 Drawing Sheets

CAPACITANCE MEASUREMENT IN A BEARING HOUSING

CROSS REFERENCE TO RELATED APPLICATION

This is a Non-Provisional Patent Application, filed under the Paris Convention, claiming the benefit of Great Britain (GB) Patent Application Number 1505264.0, filed on 27 Mar. 2015, which is incorporated herein by reference in its entirety.

TECHNOLOGICAL FIELD

The present invention relates to a bearing arrangement that provides a bearing and a capacitance sensor arranged within a housing of the bearing, which may be used to determine a degree of contamination in a grease lubricant that is present within the housing.

BACKGROUND OF THE INVENTION

To enable a long service life, it is important that a bearing is properly lubricated. Most bearings are grease lubricated, whereby oil from the grease generates an oil film during bearing operation, which separates the rolling contact surfaces. If the oil film breaks down, metal-to-metal contact occurs that can quickly lead to bearing failure if the oil film is not replenished. Monitoring methods are therefore applied in some applications to monitor the lubrication condition in a bearing, so that re-lubrication can be carried out before failure occurs. In EP1676041, for example, capacitance measurements are used to determine the film thickness of the oil film.

Lubricant contamination can also lead to early bearing failure. If an oil or grease lubricant contains abrasive particles, the rolling contact surfaces are likely to get damaged. The presence of water is also undesirable, as this can lead to surface corrosion. Water can also accelerate chemical degradation of a lubricating oil or of the thickener structure within a grease.

Therefore, in applications where a bearing might be exposed to the ingress of contamination, condition monitoring of the lubricant is sometimes applied. Capacitance measurement can be used to detect contamination. JP 2007198576, for example, discloses a sealed bearing, whereby a pair of electrodes is provided on an inner, axially oriented surface of a seal, for detecting the ingress of water.

SUMMARY OF THE INVENTION

The present invention resides in bearing arrangement providing a bearing mounted in a housing, whereby a grease lubricant is present within the housing for lubricating the bearing. The arrangement further provides a support frame at least partly made of an electrically insulating material, arranged in a space within the housing, so as to lie axially between the bearing and a housing seal. The support frame is provided with at least one electrode pair having first and second electrodes arranged such that a portion of the grease lubricant is in contact therewith. A capacitance meter is provided for measuring a capacitance between the first and second electrodes. In accordance with the invention, the support frame provides a radially oriented surface and a plurality of ribs that extend in a radially inward direction, whereby the ribs are circumferentially spaced and have a sufficient circumferential spacing to enable grease to flow between adjacent ribs. One of the first and second electrodes is provided on the radially oriented surface of the support frame or on a rib surface that faces an adjacent rib.

Preferably, the support frame provides a ring or ring segment that is mounted to the housing, whereby the ribs extend from the ring segment. The support frame may thus have a simple construction that is easy to retro-fit to an existing bearing arrangement.

In one embodiment, an electrode is provided on a radially oriented surface of the support frame; e.g. on a radially inner surface of the ring or ring segment. The electrode may be an arcuate strip of conductive material that extends in circumferential direction. This type of electrode will therefore be referred to as a circumferential electrode. Suitably, the circumferential electrode is provided between adjacent ribs. The ribs are spaced so as to allow the movement of grease in an axial direction. This is beneficial in terms of enabling used grease to exit the bearing housing when fresh grease is added. Furthermore, grease can easily pass over the circumferential electrode, thereby enabling the electrode to be cleaned by the grease.

In a further embodiment, an electrode is provided on a surface of rib that faces an adjacent rib surface. The electrode may be a strip of electrically conductive material that extends in radial direction, or the rib itself may be formed from a radially extending conductor. This type of electrode will therefore be referred to as a radial electrode. Again, grease will be able to move in an axial direction past the radial electrode, thereby enabling the electrode to be cleaned by the grease.

Thus, the benefit of a radial electrode and of a circumferential electrode is that the capacitance measured after a re-lubrication event will accurately reflect the degree of contamination in the grease. If the electrodes were placed on an axially oriented surface of the support fame, there is a risk that used grease would get stuck there.

A further advantage of a radial electrode, which extends towards a shaft that is rotationally supported in the housing by the bearing, is that grease migrates more easily through an area where there is motion. Grease will therefore tend to move along the shaft, meaning that the presence of an electrode at a radially inner location is particularly desirable for enabling capacitance measurement and detecting contamination in grease close to the shaft.

In some examples, the first electrode of at least one electrode pair is a circumferential electrode and the second electrode is a radial electrode. In other examples, the first and second electrodes are radial electrodes that are provided on or formed by adjacent ribs.

In a further embodiment, the support frame provides first and second concentrically arranged rings or ring segments, such that a radial gap exists therebetween for allowing the passage of grease. The first and second rings or ring segments are connected by the radially extending ribs. Thus, a radially outer surface of the inner ring/inner ring segment may be provided with a circumferential electrode. The electrode is thus located relatively close to the shaft, which has the same benefits as described above. In one example, the first and second electrodes of at least one electrode pair are provided on the first and second rings or ring segments respectively so as to be radially opposite each other. In other examples, one electrode of the pair is a radial electrode provided on or formed by a rib.

In a further development of the invention, the support frame is provided with multiple electrode pairs. Each rib surface that faces an adjacent rib surface may be provided with a radial electrode. A circumferential electrode may be provided between each pair of adjacent ribs. Any two electrodes which are insulated from each other may form an electrode pair, although needless to say, capacitance will be measurable only if the electrodes are sufficiently close to each other. In one example, the circumferential electrodes on the support frame are electrically connected, such that only one connection to the capacitance meter is required. The radial electrodes on the ribs are then insulated from each other and are connected individually to the capacitance meter.

The benefit of multiple electrode pairs is that it becomes possible to determine a spatial distribution of contamination levels within the housing, based on the relative location of each electrode pair and on the capacitance measured between each electrode pair. Localized areas of contamination can therefore be detected when e.g. a first capacitance measured between the first electrode pair is higher than a second capacitance measured between the second electrode pair.

Since the capacitance of the lubricant depends on the composition of the lubricant, any change in composition resulting in different dielectric properties of the lubricant leads to a change in capacitance. In particular, the dielectric constant of water is considerably higher than the dielectric constant of conventionally used bearing lubricants such as oil and grease. The presence of metal particles in the lubricant will also change its dielectric constant. The measured capacitance can also indicate a degree of humidity within the bearing housing.

During normal operation of the bearing, no significant change in capacitance is expected. A sudden increase in capacitance can indicate the ingress of water or the presence of wear debris. A sudden decrease in capacitance could be indicative of grease leakage due to seal failure.

Consequently, if a severe change in capacitance is measured, a signal can be sent to e.g. a grease pump to initiate bearing re-lubrication, before damage to the bearing occurs.

In one embodiment of the invention, the bearing arrangement further provides a temperature sensor configured to determine the temperature of the grease, which may vary significantly during bearing operation. In particular, a temperature difference can be expected when comparing a static bearing with a bearing rotating at high speed. In general, the dielectric constant of grease does not vary significantly with temperature. The dielectric constant of water, however, does vary greatly with temperature. Therefore, by measuring the temperature, a small change in capacitance which might be interpreted as small change in water content of the grease, may instead be correctly attributed to a varying temperature. Moreover, by observing the temperature-dependent capacitance, the actual water content in the grease may be more accurately determined. The temperature sensor may be any type of temperature sensor known by the skilled person.

In one embodiment, the capacitance meter provides a processor that is programmed with upper and lower threshold values for the measured capacitance. The threshold values may be determined on the basis of previous measurements on a similar bearing arrangement that is lubricated with the same grease, or may be based on theoretical calculations. Alternatively or additionally, the processor may be configured to measure capacitance at a series of time intervals and to record the difference in capacitance values between consecutive measurements in the series. A threshold value for a maximum allowable difference may be defined, which is determined, for example, on the basis of calibration measurements. The measured difference is then compared with this threshold value, to determine if the condition of the grease lubricant has been adversely affected.

Advantageously, the processor is configured to transmit a signal to a lubrication pump in the event that a threshold is exceeded, for triggering a re-lubrication action. The bearing can thus be protected from operating in conditions of poor lubrication that could damage the bearing. In addition, a maintenance alert can be sent to a technician, to check the condition of the seal and replace it if necessary.

Other advantages of the invention will become apparent from the following detailed description and accompanying drawings.

DETAILED DESCRIPTION

Figure 1:
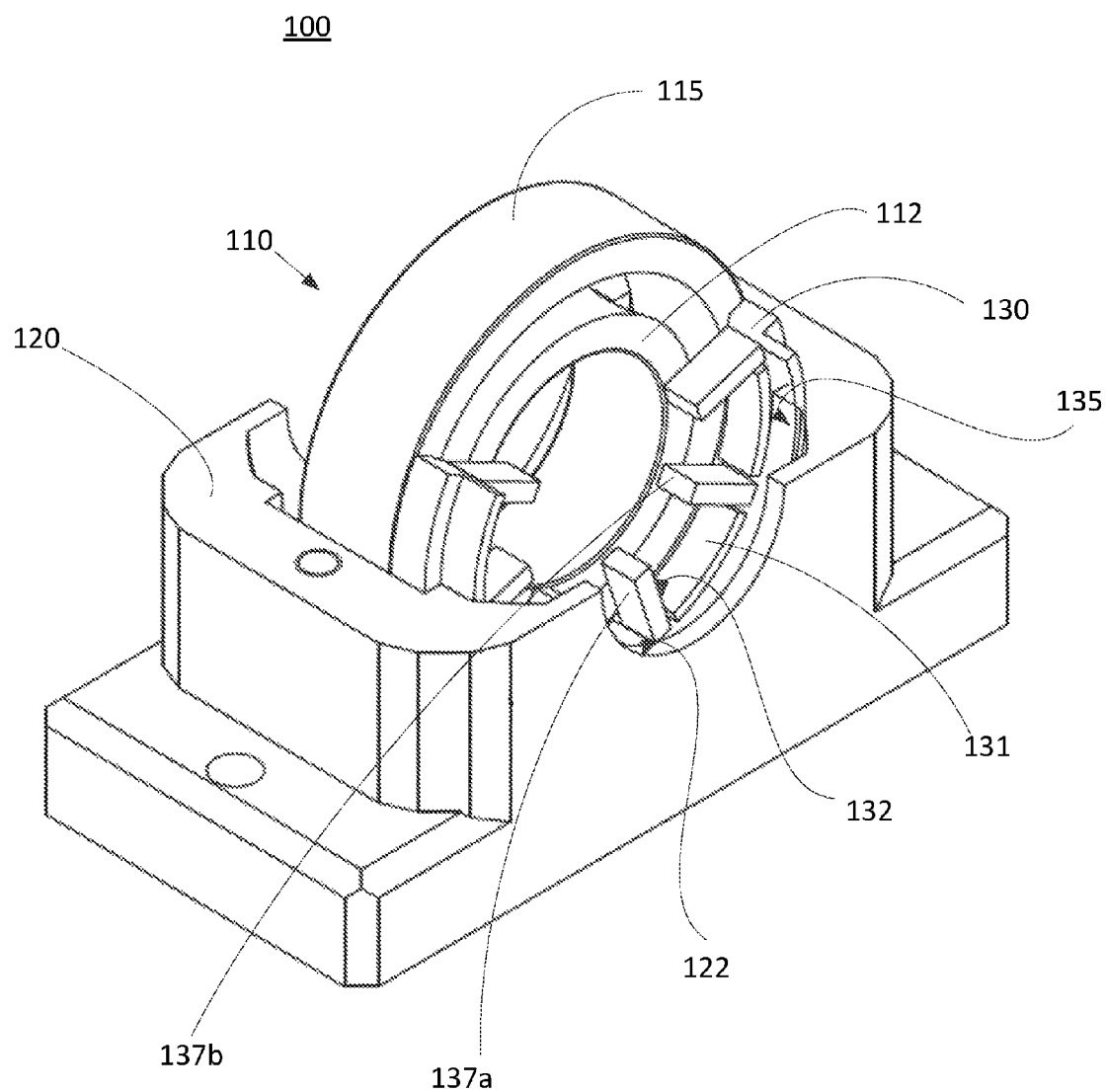
FIG. 1 shows a perspective view of parts of a bearing arrangement according to an embodiment of the invention, the arrangement providing a first example of a support frame with conductive electrodes.

In the present detailed description, various embodiments of a bearing arrangement according to the present invention are discussed with reference to a spherical roller bearing. It should be noted that this by no means limits the scope of the present invention, which is equally applicable to any type of bearing that is mounted in a housing and is lubricated with grease.

FIG. 1a shows an embodiment of a bearing arrangement 100 according to the invention, providing a spherical roller bearing 110 that is mounted in a housing 120. An upper half of the housing has been removed from the drawing, to better reveal the component parts of the inventive bearing arrangement.

The bearing 110 provides an inner ring 112, an outer ring 115 and a number of spherical rollers and a cage (not shown) disposed between an inner raceway on the inner ring 112 and an outer raceway on the outer ring 115. In use, the bearing rotationally supports a shaft (not shown) relative to the housing 120. Typically, a radial seal is provided between a bore 122 of the housing and the shaft, for preventing the ingress of contaminants into the housing and for retaining a grease lubricant (not shown) within the housing.

In applications where the bearing operates in a highly contaminated environment, it is not always possible to prevent the ingress of contaminants, such as moisture. To ensure that the contamination does not reach a level that would seriously affect the lubricating ability of the grease or damage the bearing, the bearing arrangement 100 is provided with a contamination sensor, executed as a capacitance sensor.

The capacitance sensor provides at least one electrode pair having first and second electrodes 131, 132 which are connected to a capacitance meter (not shown). The first and second electrodes are provided on a support frame 130 that is at least partly made from an electrically insulating material e.g. a polymer material. The support frame is mounted to the housing 120 and is arranged between the bearing 110 and the housing bore 122, such that the first and second electrodes of the capacitance sensor can make contact with the grease lubricant.

The capacitance measured between the first and second electrodes depends on the dielectric constant of a dielectric material present between the electrodes. When grease is the dielectric, its dielectric constant changes if the grease contains moisture or e.g. metal particles. Measuring capacitance therefore provides an indication of the degree of contamination in the grease. If the measured amount exceeds a predefined threshold, an alarm is activated. Suitably, the alarm triggers a re-lubrication event, which may be performed manually by a maintenance technician or, if the bearing arrangement is connected to a lubrication pump, the alarm causes the lubrication pump to automatically deliver a prescribed amount of grease to the bearing arrangement 100.

Typically, the upper part of the bearing housing 120 provides a grease nipple for delivering fresh grease into the bearing arrangement. As the fresh grease is delivered, the used grease is forced out of the bearing arrangement, either through the seals, or an exit hole in a lower part of the housing 120, or a combination of both. It is therefore important that the capacitance sensor does not obstruct the flow of grease within the bearing housing.

In a bearing arrangement according to the invention, the support frame is designed to enable the flow of grease in axial direction.

In the depicted embodiment, the support frame 130 provides a ring segment that is essentially C-shaped, which has a radially oriented surface 135 from which a number of ribs 137a, 137b extend in a radially inward direction. NB only two of the ribs have been provided with a reference numeral so as not to obscure the drawing. The ribs are circumferentially spaced, whereby the spacing between adjacent ribs 137a, 137b is sufficient to enable the flow of grease. Suitably, the spacing is at least 0.5 cm, if the bearing arrangement provides a small bearing. Preferably, the circumferential spacing between adjacent ribs 137a, 137b is greater than 1 cm.

The first electrode 131 is provided on the radially oriented surface 135 of the support frame 130, between two adjacent ribs 137a, 137b, and may be executed as an arcuate strip of electrically conductive material that extends circumferentially between adjacent ribs. This type of electrode will be referred to as a circumferential electrode. The second electrode 132 is provided on a surface of a rib 137a that faces towards an adjacent rib 137b. The second electrode 132 extends in radial direction and this type of electrode will be referred to as a radial electrode.

In the depicted embodiment, the first and second electrodes are arranged perpendicularly next to each other. The capacitance of a portion of grease that is located between the circumferential electrode 131 and the radial electrode 132 is measurable in order to detect contamination. Suitably, the circumferential electrode 131 and the radial electrode 132 also extend in the axial direction of the bearing, i.e. have an axial width. This increases the surface area of the electrodes, which improves the resolution of the capacitance measurement.

The radial electrode 132 extends towards the shaft and is therefore able to be in contact with grease that has a radially inner location within the housing. This is beneficial, as grease flows more readily towards an area where motion occurs. Since this is the area which specifically requires lubrication, the detection of contamination close to the shaft is particularly important, so that a re-lubrication event can be triggered before the contaminated grease reaches the bearing 110.

As mentioned, the support frame is designed to enable the flow of grease in axial direction, so that grease is neither restricted from reaching the bearing nor from exiting the bearing housing after a re-lubrication event. A further advantage of the design is that the electrodes are arranged on surfaces that the grease can flow over, in the case of the circumferential electrode, and flow past in the case of the radial electrodes. As a result, fresh grease that is pumped into the housing will dislodge used grease that adheres to the electrodes 131, 132. In other words, a re-lubrication event cleans the electrodes, so that subsequent capacitance measurements accurately reflect the level of contamination.

In the arrangement shown in FIG. 1, a circumferential electrode 131 is provided between each pair of adjacent ribs 137a, 137b and a radial electrode 132 on each rib surface that faces towards an adjacent rib. Suitably, one group of electrodes e.g. the circumferential electrodes are electrically connected together, such that only one connection to the capacitance meter is required. The other group of electrodes, i.e. the radial electrodes are isolated from each other (and from the circumferential electrodes) and are connected individually to the capacitance meter. Thus, multiple pairs of first and second electrodes 131, 132 can be formed.

The use of multiple electrode pairs enables localized areas of contamination to be identified. In embodiments where the bulk capacitance of the grease is measured, there is a risk that the measured value will indicate that the grease is in an acceptable condition, despite containing an area of localized contamination. This contaminated portion of grease might reach the bearing. Therefore, the capacitance meter is preferably configured to trigger a re-lubrication action if the measured capacitance between any of the electrode pairs exceeds a predefined threshold.

Figure 2:
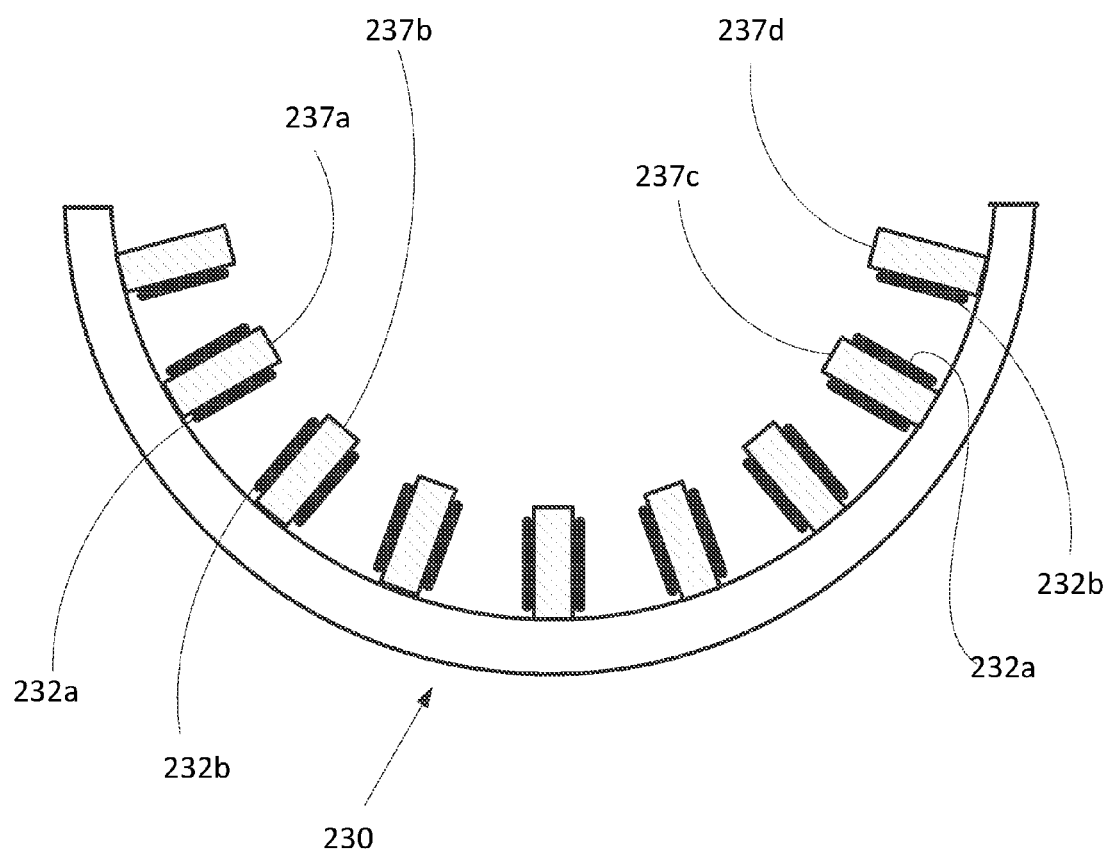
FIG. 2 shows a side view of a second example of a support frame with conductive electrodes.

A further example of a support frame with multiple electrode pairs is depicted in FIG. 2. The support frame 230 provides a ring segment from which a number of ribs 237a, 237b, 237c, 237d extend in radially inward direction. Radial electrodes 232a, 232b are provided on the surfaces of adjacent ribs that face towards each other. Again, not all ribs and electrodes have been numbered so as not to obscure the drawing.

A first rib 237a is provided with a first radial electrode 232a that faces in anticlockwise direction; an adjacent second rib 237b is provided with a second radial electrode 232b that faces in clockwise direction. In use, the first and second radial electrodes 232a, 232b form an electrode pair that is connected to a capacitance meter. At least a second electrode pair is formed by a first radial electrode 232a provided on a third rib 237c that faces towards a second radial electrode 232b provided on a fourth rib 237d. Suitably, each set of adjacent ribs is provided with radial electrodes that face towards each other. One set of radial electrodes e.g. the clockwise-facing electrodes 232b may be connected together electrically while the other set, i.e. the anticlockwise-facing electrodes 232a, are electrically insulated from each other and connected individually to the capacitance meter, so as to form multiple electrode pairs. It is thus possible to measure capacitance at multiple locations within the housing, to more accurately detect areas of localized contamination within the grease lubricant.

The radial electrodes 232a, 232b of support frame shown in FIG. 2 also enable capacitance measurement of grease that has a radially inner location within the housing, due to their radial extension. Suitably, the electrodes also have an axial extension, so as to increase their surface area.

Figure 3:
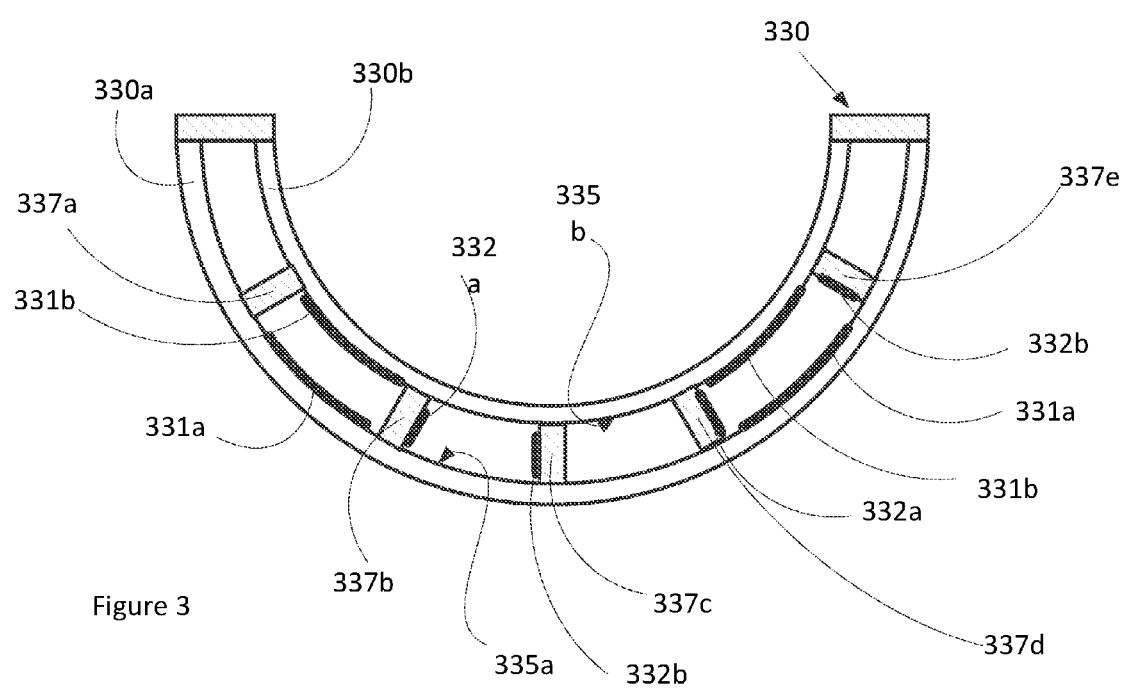
FIG. 3 shows a side view of a third example of a support frame with conductive electrodes.

A further example of a support frame with multiple electrode pairs is depicted in FIG. 3. The support frame 330 is made of an electrically insulating material and provides a first ring segment 330a, adapted for mounting to the lower part of a bearing housing. The support frame further provides a second ring segment 330b, concentrically arranged relative to the first ring segment 330a, whereby a radial gap exists between the segments. The radial gap allows grease to move in an axial direction between the ring segments. The first and second ring segments are connected by radially extending ribs 337a, 337b, 337c, 337d which are circumferentially spaced to allow the passage of grease.

In this example, the first ring segment 330a has a radially oriented surface 335a provided with a circumferential electrode 331a between adjacent ribs 337a and 337b. The second ring segment 330b has a radially oriented surface 335b provided with a circumferential electrode 331b between adjacent ribs 337a and 337b. These radially opposite circumferential electrodes are connected to a capacitance meter and form an electrode pair for measuring capacitance in radial direction. The circumferential electrode 331b on the second ring segment 330b is located relatively close to the shaft, which, as explained above, is a beneficial location for measuring capacitance.

A second pair of electrodes is formed by first and second radial electrodes 332a, 332b which are provided on facing surfaces of adjacent ribs 337b and 337c. The support frame 330 further provides two circumferential electrodes 331a, 331b which are respectively provided on the first 330a and second 330a ring segments, between adjacent ribs 337d and 337e. In addition, adjacent ribs 337d and 337e are provided with radial electrodes 332a and 332b that face each other. One electrode pair is formed by the radial electrode on rib 337d and the adjacent circumferential electrode 331b on the second ring segment 330b. Another electrode pair is formed by the radial electrode on rib 337e and the adjacent circumferential electrode 331a on the first ring segment. As will be understood, other combinations are possible.

The capacitance of the grease in contact with the various electrodes can thus be measured not only at different locations, but also in different directions, enabling an accurate determination of the spatial distribution of contamination within the grease lubricant.

A number of aspects/embodiments of the invention have been described. It is to be understood that each aspect/embodiment may be combined with any other aspect/embodiment. Moreover the invention is not restricted to the described embodiments, but may be varied within the scope of the accompanying patent claims.

The invention claimed is:

1. A bearing arrangement comprising:
   a bearing mounted in a housing, the bearing having an inner ring an outer ring and a plurality of rolling elements arranged between the inner and outer rings;
   a grease lubricant provided inside the bearing arrangement; and
   a contamination sensor for detecting a level of contamination of the grease lubricant, the contamination sensor comprising a capacitance meter and a support frame mounted to the housing at an axial side of the bearing, wherein:
      the support frame is provided with an electrode pair having first and second electrodes that are connected to the capacitance meter and are arranged to be in contact with a portion of the grease lubricant;
      the support frame provides a radially oriented surface and a plurality of ribs that extend in a radially inward direction, the plurality of ribs being circumferentially spaced and having a sufficient circumferential spacing to enable grease to flow between adjacent ribs; and
      at least one of the first and second electrodes is provided on the radially oriented surface of the support frame or on a rib surface that faces an adjacent rib.

2. The bearing arrangement according to claim 1, wherein the first electrode is a circumferentially extending electrode provided on the radially oriented surface of the support frame between adjacent ribs and wherein the second electrode is a radially extending electrode provided on one of the adjacent rib surfaces that face each other.

3. The bearing arrangement according to claim 1, wherein the first and second electrodes are radially extending electrodes provided on adjacent rib surfaces that face each other.

4. The bearing arrangement according to claim 1, wherein the support frame is provided with a plurality of electrode pairs, each pair having first and second electrodes.

5. The bearing arrangement according to claim 4, wherein the support frame provides a plurality of radially extending electrodes and a plurality of circumferentially extending electrodes.

6. The bearing arrangement according to claim 5, wherein a first electrode pair is formed by two radial electrodes provided on surfaces of adjacent ribs that face each other, and a second electrode pair is formed by a radial electrode and circumferential electrode that is adjacent to and arranged perpendicularly to the radial electrode.

7. The bearing arrangement according to claim 1, further comprising a grease pump connected to the bearing arrangement, the pump being configured to deliver a prescribed volume of grease to the bearing arrangement when a capacitance value is measured between an electrode pair that exceeds a predefined threshold.

8. The bearing arrangement according to claim 1, wherein the support frame provides one of a ring and ring segment mounted to the housing.

9. The bearing arrangement according to claim 8, wherein the support frame provides first and second concentrically arranged rings or ring segments that are connected by the ribs, such that a radial gap exists between the rings or ring segments for allowing the passage of grease, and wherein the first and second electrodes are provided on radially opposite surfaces of the first and second rings or ring segments.

10. The bearing arrangement according to claim 9, wherein the support frame provides a further electrode pair formed by two radial electrodes provided on surfaces of adjacent ribs that face each other.

11. The bearing arrangement according to claim 9, wherein the support frame provides a further electrode pair formed by a radial electrode and circumferential electrode that is adjacent to and arranged perpendicularly to the radial electrode.

12. The bearing arrangement according to claim 9, wherein the support frame includes a second electrode pair formed by two radial electrodes provided on surfaces of adjacent ribs that face each other, and further includes a third electrode pair formed by a radial electrode and a circumferential electrode that is adjacent to and arranged perpendicularly to the radial electrode.

* * * * *